United States Patent [19]

Shiraishi et al.

[11] 3,970,702
[45] July 20, 1976

[54] CATALYTIC PROCESS FOR THE PREPARATION OF ACROLEIN

[75] Inventors: Tatsuo Shiraishi; Susumu Kishiwada; Shinkichi Shimizu; Shigern Honmaru; Hiroshi Ichihashi; Yoshihiko Nagaoka, all of Niihama, Japan

[73] Assignee: Sumitomo Chemical Company, Limited, Japan

[22] Filed: Dec. 3, 1974

[21] Appl. No.: 529,100

Related U.S. Application Data

[63] Continuation of Ser. No. 159,306, July 2, 1971, abandoned.

[30] Foreign Application Priority Data

| July 3, 1970 | Japan | 45-58503 |
| July 6, 1970 | Japan | 45-59298 |
| July 8, 1970 | Japan | 45-60042 |
| Aug. 15, 1970 | Japan | 45-71609 |
| Sept. 11, 1970 | Japan | 45-80174 |

[52] U.S. Cl. .................................... 260/604 R
[51] Int. Cl.² ................................... C07C 45/04
[58] Field of Search ........................ 260/604 R

[56] References Cited
UNITED STATES PATENTS

| 3,236,782 | 2/1966 | Koch | 260/604 R |
| 3,248,340 | 4/1966 | Callahan et al. | 260/604 R |
| 3,576,764 | 4/1971 | Yamaguchi et al. | 260/604 R |

FOREIGN PATENTS OR APPLICATIONS

| 446,245 | 3/1969 | Japan | 260/604 R |

Primary Examiner—James O. Thomas, Jr.
Assistant Examiner—W. B. Lone
Attorney, Agent, or Firm—Stewart and Kolasch, Ltd.

[57] ABSTRACT

A catalytic process for the preparation of acrolein by the vapor phase oxidation of propylene which comprises contacting propylene and oxygen with a catalyst composition comprising a catalyst system of the formula:

$$Mo_a\ Bi_b\ Fe_c\ X_d\ Ni_e\ Tl_f\ P_g\ O_h$$

wherein X is one or more of Mg, Mn and Co and $a$, $b$, $c$, $d$, $e$, $f$, $g$ and $h$ represent, respectively, the number of atoms wherein $a$ is 12, $b$ is 0.1 to 5, $c$ is 0.1 to 5, $d$ is 0 to 12, $e$ is 0.1 to 12, $f$ is 1 or less but not 0, $g$ is 0 to 5 and $h$ depends on the number of the other atoms and is usually from 36 to 89. Acrolein is produced with the use of said catalyst in a high selectivity and an excellent yield per each pass even at a large space velocity.

11 Claims, 1 Drawing Figure

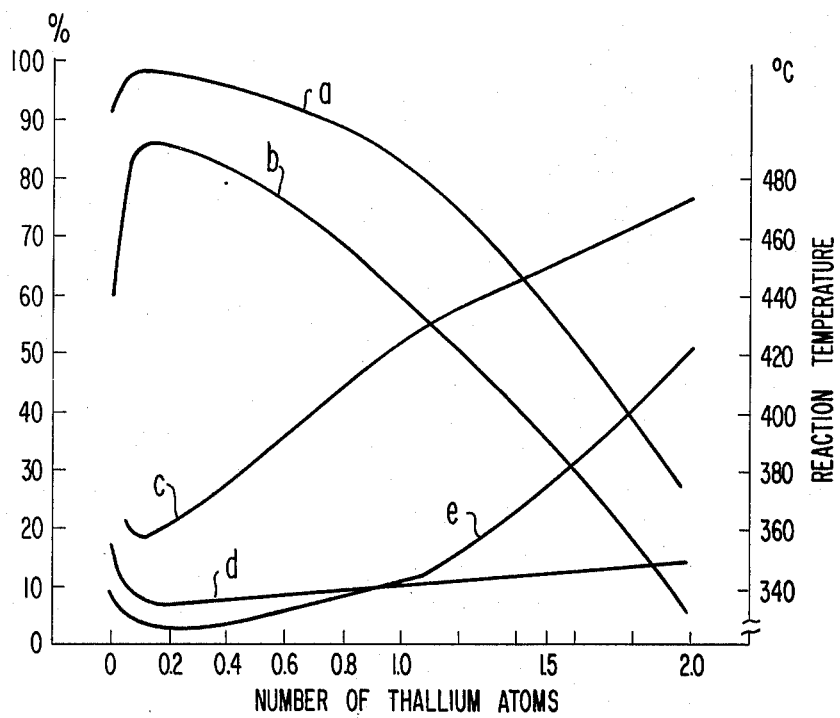

CATALYTIC PROCESS FOR THE PREPARATION OF ACROLEIN

This application is a continuation of copending app. Ser. No. 159,306 filed on July 2, 1971 now abandoned.

The present invention relates to a catalytic process for the preparation of acrolein. More particularly, it relates to a process for the preparation of acrolein by the catalytic oxidation of propylene with oxygen in the presence of a specific catalyst system.

It is generally known that, in the vapor phase catalytic oxidation of olefinic hydrocarbons to the corresponding unsaturated aldehydes, the selection of appropriate catalysts and suitable reaction conditions is essential for realizing a high conversion of the starting olefinic hydrocarbons and an excellent selectivity to the objective unsaturated aldehydes at large space velocities. In the production of acrolein from propylene, however, the elevation of the reaction temperature so as to attain a higher conversion of of propylene usually results in the marked depression of the selectivity to acrolein. Because of this reason, a high yield of acrolein has been hitherto obtained not by adopting a high reaction temperature but by maintaining a low space velocity, insofar as conventional catalyst compositions are employed.

For the vapor phase oxidation of olefinic hydrocarbons, there have been proposed various catalyst compositions which comprise multi elements in the oxide form, among which a catalyst system comprising Mo, Bi, P, Fe, at least one of Co and Ni, and O is particularly well known in view of the excellent conversion of the starting olefinic hydrocarbons [U.S. Pat. No. 3,454,630; U.S. Pat. No. 3,522,299; German Pat. No. 1,268,609; French Pat. No. 1,514,167; Japanese patent publication No. 2324/1968; Japanese patent publication No. 5855/1969; Japanese patent publication No. 6245/1969, etc.]. When such catalyst compositions are applied to the vapor phase oxidation of propylene to acrolein, a high conversion of propylene and a high selectivity to acrolein will be simultaneously attained if the space velocity is relatively small. In case of the space velocity being made larger, however, the selectivity to acrolein is remarkably decreased. Thus, even these particular catalyst compositions are not exceptional.

Apart from and in addition to the above disadvantage, the use of conventional catalyst compositions in the oxidation of olefinic hydrocarbons with high space velocities at elevated temperatures so as to increase the conversion of the olefinic hydrocarbons results in the by-production of carbon monoxide, carbon dioxide and the like in large amounts with marked generation of heat, whereby the control of the reaction conditions is made difficult.

As the result of the study seeking a catalyst composition which can oxidize propylene to acrolein in a high conversion and an excellent selectivity even at a high space velocity with a long catalytic life, it has been found that a catalyst system comprising Mo, Bi, Fe, one of Mg and Mn, Ni, P and O, and a catalyst system comprising Mo, Bi, Fe, at least two of Mg, Mn and Co, Ni, P and O (hereinafter referred to as "non-Tl catalyst system") meet such requirements. It has also been found that the incorporation of Tl into such a catalyst system can suppress markedly the production of by-products such as carbon monoxide, carbon dioxide and acrylic acid as recognized in the use of the non-Tl catalyst system while maintaining the said favorable catalytic properties. This invention is based on these findings.

According to the present invention, there is provided a process for the vapor phase catalytic oxidation of propylene which comprises contacting propylene and oxygen with a catalyst composition comprising a catalyst system of the formula: $Mo_aBi_bFe_cX_dNi_eTl_fP_gO_h$ wherein X is one or more of Mg, Mn, and Co and $a$, $b$, $c$, $d$, $e$, $f$, $g$ and $h$ represent respectively the number of atoms, provided that, in case of $a$ being 12, $b$ is 0.1 to 5 (preferably 0.5 to 3), $c$ is 0.1 to 5 (preferably 0.5 to 5), $d$ is 0 to 12 (preferably 0 to 9), $e$ is 0.1 to 12 (preferably 1.5 to 12), $f$ is 1 or less but not 0 (preferably 0.01 to 0.5), $g$ is 0 to 5 (preferably 0.01 to 2) and $h$ is decided depending on the number of the other atoms and is usually from 36 to 89 (preferably 39.1 to 74.8) (hereinafter referred to as "Tl catalyst system") to produce acrolein in a high selectivity and an excellent yield per each pass.

The catalyst composition used in the present invention is quite characteristic in containing a small amount of thallium. Compared with the non-Tl catalyst system, the Tl catalyst system suppresses markedly the by-production of carbon monoxide, carbon dioxide and the like so that the selectivity to acrolein is highly increased. Attention is, however, directed to the fact that the incorporation of thallium in excess rather results in the inhibition of the production of acrolein. From these facts, it may be assumed that the catalytic mechanism of the Tl catalyst system is different from that of the non-Tl catalyst system and the thallium component in the Tl catalyst system is present not in a mere oxide form but in a certain complex compound form. The said assumption can be supported also by the fact that, while thallium oxide is apt to be reduced in a reductive atmosphere to the lower oxide form or metallic thallium of high volatility, the Tl catalyst system does not materially lose its catalytic activity even after use in a continuous oxidation for more than 1000 hours and the nonvolatilization of the thallium component therein is confirmed by the fluorescent X ray analysis.

The starting materials in the vapor phase oxidation of this invention are propylene and oxygen. As the oxygen source, there may be used pure oxygen gas, air enhanced or not in oxygen concentration or any other oxygen-containing gas. From the economical viewpoint, the use of air is preferred. As the case may be, steam is introduced into the reaction system. If desired, an appropriate inert gas such as nitrogen, carbon dioxide or argon may be used as a diluent. The molar ratio of propylene and oxygen may be within a range of 1:0.4–3. When steam is introduced, it may be used in a rate of 1 to 15 mol to 1 mol of propylene. In general, the preferred molar ratio of propylene, oxygen and steam is 1:1–3:3–10.

For preparation of the catalyst system, there may be employed molybdenum compounds (e.g. ammonium molybdate, molybdenum oxide, molybdic acid), bismuth compounds (e.g. bismuth nitrate, bismuth oxide), iron compounds (e.g. ferric nitrate, iron oxide), nickel compounds (e.g. nickel nitrate, nickel oxide), manganese compounds (e.g. manganese nitrate, manganese oxide), magnesium compounds (e.g. magnesium nitrate, magnesium oxide), cobalt compounds (e.g. cobalt nitrate, cobalt oxide), thallium compounds (e.g. thallium nitrate, thallium oxide, thallium phosphate)

and phosphorus compounds (e.g. phosphoric acid, ammonium phosphate).

The preparation of the catalyst composition may be executed by a per se conventional procedure. For instance, a thallium salt, an iron salt, a bismuth salt, a phosphorus compound, a nickel salt and one or more of a manganese salt, a magnesium salt and a cobalt salt are added to an aqueous solution of a molybdate such as ammonium molybdate, the resulting slurry is admixed with a carrier material and evaporated to dryness, and the resultant cake is calcined at an elevated temperature in the atmosphere and, after cooling, crushed and shaped into pellets or granules.

The catalyst system may be used as such but is favorably incorporated with a suitable carrier (e.g. silica, alumina, silicon carbide, titanium oxide). The amount of the carrier is varied with its kind and may be usually less than 90 % by weight, preferably from 5 to 90 % by weight, of the catalyst composition.

The production of acrolein using the catalyst composition of the invention may be effected by a fluidized bed process or a fixed bed process. The particle size of the catalyst composition is not particularly limited and may be optionally varied with the type of its use. The reaction temperature is associated with the kind of the catalyst composition and is usually from 200° to 550°C, preferably from 250° to 500°C. The reaction pressure may be around atmospheric pressure, preferably 0.7 to 5 absolute atm. The space velocity is ordinarily from 100 to 12,000 liter.gas/liter.catalyst/hr, preferably from 200 6,000 liter.gas/liter.catalyst/hr.

By the use of the catalyst system of the present invention, acrolein can be produced with a high selectivity in an excellent yield per each pass even at a large space velocity, and the formation of by-products such as carbon oxides is considerably suppressed. Further, the space time yield of acrolein is high, showing an excellent productivity of the catalyst system. In addition, the life of the catalytic activity is sufficiently and satisfactorily long, and thallium in the catalyst composition is never volatilized during the reaction.

Some of the advantages brought by the use of the Tl catalyst system, compared with the use of the non-Tl catalyst system, are as follows:

1. The Tl catalyst system is much higher (e.g. 10 % more) in the conversion of propylene.
2. The by-production of excessively oxidized substances is extremely suppressed in case of using the Tl catalyst system and, therefore, the selectivity to acrolein is much higher. This advantage is seen not only at a relatively small space velocity but also at a relatively large space velocity.
3. Since the by-production of excessively oxidized substances is suppressed, the generation of heat is small and the temperature distribution in the catalyst bed is also small, whereby the regulation of the reaction conditions can be made with facility.
4. As the by-production of excessively oxidized substances is suppressed, the purification of the produced acrolein can be made easier.
5. The Tl catalyst system is highly active even at a lower temperature, and it can be used with a longer catalytic life.

Practical and presently preferred embodiments of the present invention are illustrately shown in the following examples, wherein the conversion of propylene, the selectivity to the product, the yield of the product and the space velocity are calculated respectively according to the equations:

$$\text{Conversion of propylene (\%)} = \frac{\text{Reacted propylene (mol)}}{\text{Feed propylene (mol)}} \times 100$$

$$\text{Selectivity (\%)} = \frac{\text{Weight of carbon atoms in product}}{\text{Weight of carbon atoms in reacted propylene}} \times 100$$

$$\text{Yield of product (\%)} = (\text{Conversion of propylene}) \times (\text{Selectivity}) \times \frac{1}{100}$$

$$\text{Space velocity} = \frac{\text{Flow volume of feed gas per hour (liter.gas/hr)}}{\text{Volume of catalyst (liter.catalyst)}}$$

EXAMPLE 1

A solution of bismuth nitrate (12.13 g) in a mixture of concentrated nitric acid (4 ml) and water (30 ml) and a solution of ferric nitrate (20.20 g), magnesium nitrate (9.62 g), cobalt nitrate (10.92 g), nickel nitrate (43.70 g) and thallium nitrate (0.67 g) in water (250 ml) are combined together. To the resultant mixture, a solution of ammonium molybdate (52.98 g) and concentrated phosphoric acid (85 % by weight; 2.88 g) in a mixture of aqueous ammonia (28 % by weight; 30 ml) and water (300 ml) is added, and the mixture is stirred well to make a slurry dispersion. Then silica sol ($SiO_2$, 20 % by weight; 100 ml) is added thereto under vigorous stirring. The resultant slurry dispersion is evaporated by dryness, and the residue is calcined at 300°C for 3 hours (1st calcination), cooled and crushed. The obtained powder is tableted and calcined at 525°C for 6 hours in the atmosphere (2nd calcination) to give a catalyst composition, of which the active components correspond to the formula: $Mo_{12}Bi_1Fe_2Mg_{1.5}Co_{1.5}Ni_6Tl_{0.1}P_1O_{52.2}$ (wherein the carrier components are omitted).

In a glass-made reaction tube of 12 mm in inner diameter, the catalyst composition as obtained above and crushed to granules of 10 to 16 mesh (8.0 ml) is charged and heated. Then, a gaseous mixture of propylene, air and steam (1:7:7 in molar ratio) is introduced into the reaction tube at 355°C and at a space velocity of 1200 liter.gas/liter.catalyst/hr, whereby acrolein is produced. The conversion of propylene is 97.6 %, the selectivity to acrolein is 87.2 % and the yields of acrolein, acrylic acid, acetic acid, acetaldehyde, carbon dioxide and carbon monoxide are respectively 85.1 %, 7.4 %, 0.7 %, less than 0.2 %, 2.0 % and 1.1 %. The space time yield of acrolein is 3.04 mol/liter.catalyst/hr.

EXAMPLE 2

As in Example 1, there are prepared some catalyst compositions of which the active components correspond to the formula: $Mo_{12}Bi_1Fe_2Mg_{1.5}Co_{1.5}Ni_6Tl_fP_1O_h$ wherein $f$ is 0 and 2 and $h$ is 52.0 to 55.0, i.e. (1) $Mo_{12}Bi_1Fe_2Mg_{1.5}Co_{1.5}Ni_6P_1O_{52.0}$, (2) $Mo_{12}Bi_1Fe_2Mg_{1.5}Co_{1.5}Ni_6Tl_{0.02}P_1O_{52.03}$, (3) $Mo_{12}Bi_1Fe_2Mg_{1.5}Co_{1.5}Ni_6Tl_{0.05}P_1O_{52.08}$, (4) $Mo_{12}Bi_1Fe_2Mg_{1.5}Co_{1.5}Ni_6Tl_{0.1}P_1O_{52.15}$, (5) $Mo_{12}Bi_1Fe_2Mg_{1.5}Co_{1.5}Ni_6Tl_{0.2}P_1O_{52.30}$, (6) $Mo_{12}Bi_1Fe_2Mg_{1.5}Co_{1.5}Ni_6Tl_{0.3}P_1O_{52.45}$, (7) $Mo_{12}Bi_1Fe_2Mg_{1.5}Co_{1.5}Ni_6Tl_1P_1O_{53.50}$ and (8) $Mo_{12}Bi_1Fe_2Mg_{1.5}Co_{1.5}Ni_6Tl_2P_1O_{55.0}$. A mixture of propylene, air and steam in a molar ratio of 1:7:7 is contacted with the above prepared catalyst composition at a space velocity of 1200 liter.gas/liter.catalyst/hr as in Example 1. The results are shown in the FIGURE of the attached drawings wherein the number of thallium atoms (f) is indicated on the axis of the abscissa, the percent is shown on the axis of the ordinate of the left side and the reaction temperature is represented on the axis of the ordinate on the right side. The curves a, b, c, d and e represent respectively the conversion of proplyene, the yield of acrolein, the reaction temperature, the yield of acrylic acid and the total yield of carbon monoxide and carbon dioxide.

From the FIGURE, it can be seen that the catalyst composition (1) ($f = 0$) requires a temperature of 400°C for attaining a conversion of proplyene more than 90 %, the increase of the thallium content in the catalyst compositions results in lowering the reaction temperature to be required for attaining the same result as above and the catalyst composition (4) ($f = 0.1$) shows a 97.6 % conversion of propylene even at a temperature of 355°C. But, a higher increase of the thallium content in the catalyst composition requires a higher reaction temperature for attaining a conversion of propylene more than 90 % and, when the catalyst compositions (7) ($f = 1.0$) and (8) ($f = 2.0$) are used, the conversion of propylene is extremely decreased.

It can be also seen that the yield of acrolein in case of using the catalyst composition (1) ($f = 0$) is 59.5 %, the increase in the thallium content results in a marked elevation of the yield and the highest yield attains 85.1 % in case of using the catalyst composition (4) ($f = 0.1$). A higher content of thallium produces the decreased yield of acrolein and, in case of using a catalyst compositions (7) ($f = 1.0$) and (8) ($f = 2.0$), the yield of acrolein is extremely inferior.

It can be further seen that the by-production of acrylic acid, carbon monoxide and carbon dioxide is contrary to the above results. Namely, the catalyst composition (1) ($f = 0$) affords acrylic acid in a 18.4 % yield and carbon monoxide and carbon dioxide in a 9.2% total yield. The inclusion of thallium results in the remarkable decrease of these yields and, in case of using the catalyst composition (4) ($f = 0.1$), the yield of acrylic acid and the total yield of carbon monoxide and carbon dioxide are respectively 7.4 % and 3.1 %.

EXAMPLES 3 TO 26

In the same manner as in Example 1 but using various catalyst compositions, the vapor phase oxidation of propylene to acrolein is carried out. The results are shown in Table 1.

Table 1

| Ex. No. | Catalyst composition | | | | | | | | | | Reaction condition | | Propylene conversion (%) | Yield (%) | | | | Space time yield (mol/l/hr) |
|---|---|---|---|---|---|---|---|---|---|---|---|---|---|---|---|---|---|---|
| | Mo | Bi | Fe | Mg | Co | Mn | Ni | Tl | P | O | Reaction temp. (°C) | Space velocity (1/l/hr) | | Acrolein | Acrylic acid | CO$_2$ | CO | others | |
| 3 | 12 | 1 | 1 | 0 | 0 | 0 | 8.5 | 0.2 | 0.1 | 48.1 | 375 | 1200 | 96.1 | 78.4 | 9.8 | 1.0 | 1.0 | HAc 0.8 AAl 0.2 | 2.80 |
| 4 | 12 | 1 | 1 | 0 | 0 | 0 | 8.5 | 0.05 | 0.1 | 47.8 | 375 | 1200 | 95.7 | 75.2 | 12.5 | 2.5 | 1.8 | | 2.69 |
| 5 | 12 | 2 | 2 | 0 | 0 | 0 | 5.5 | 0.2 | 0.1 | 48.1 | 375 | 1200 | 93.1 | 75.9 | 10.1 | 1.3 | 1.2 | | 2.71 |
| 6 | 12 | 2 | 2 | 0 | 0 | 0 | 7.5 | 0.2 | 1 | 52.3 | 375 | 1200 | 90.3 | 74.7 | 7.7 | 2.0 | 1.2 | | 2.67 |
| 7 | 12 | 1 | 1 | 4 | 0 | 0 | 4.5 | 0.05 | 0.1 | 47.8 | 400 | 1200 | 92.3 | 74.3 | 9.6 | 1.9 | 1.7 | | 2.65 |
| 8 | 12 | 1 | 1 | 4 | 0 | 0 | 4.5 | 0.2 | 0.1 | 48.1 | 400 | 1200 | 95.4 | 78.2 | 10.6 | 1.5 | 1.2 | HAc 1.1 AAl 0.2 | 2.79 |
| 9 | 12 | 1 | 1 | 2 | 0 | 0 | 6.5 | 0.2 | 0.1 | 48.1 | 375 | 1200 | 94.8 | 75.4 | 11.4 | 1.7 | 1.2 | | 2.69 |
| 10 | 12 | 2 | 2 | 2.5 | 0 | 0 | 3 | 0.1 | 0.1 | 47.9 | 400 | 1200 | 90.2 | 73.8 | 9.2 | 1.6 | 1.3 | | 2.64 |
| 11 | 12 | 1 | 1 | 0 | 2 | 0 | 7 | 0.1 | 1 | 50.7 | 360 | 1200 | 95.4 | 84.8 | 5.8 | 1.3 | 0.5 | | 3.03 |
| 12 | 12 | 1 | 1 | 0 | 2 | 0 | 7 | 0.1 | 1 | 50.7 | 325 | 400 | 96.2 | 81.5 | 7.7 | 2.2 | 1.5 | | 0.97 |
| 13 | 12 | 1 | 1 | 0 | 2 | 0 | 7 | 0.1 | 1 | 50.7 | 425 | 4800 | 89.1 | 72.3 | | | | | 10.29 |
| 14 | 12 | 1 | 1 | 0 | 4 | 0 | 4.5 | 0.1 | 0.08 | 47.9 | 365 | 1200 | 97.6 | 82.5 | 9.3 | 2.1 | 0.9 | | 2.94 |
| 15 | 12 | 1 | 1 | 0 | 0.3 | 0 | 10 | 0.1 | 1 | 52.0 | 375 | 1200 | 95.8 | 83.0 | 8.2 | | | | 2.95 |
| 16 | 12 | 1 | 1 | 0 | 0 | 2 | 6.5 | 0.2 | 0.1 | 48.1 | 375 | 1200 | 96.3 | 78.6 | 11.0 | 2.5 | 1.8 | HAc 0.9 AAl 0.2 | 2.81 |
| 17 | 12 | 2 | 1 | 0 | 0 | 3 | 4 | 0.1 | 0.1 | 47.9 | 400 | 1200 | 91.2 | 74.1 | 10.3 | | | | 2.65 |
| 18 | 12 | 1 | 1 | 1 | 1 | 1 | 5.5 | 0.2 | 0.1 | 48.1 | 375 | 1200 | 97.5 | 84.2 | 7.9 | 1.7 | 0.9 | HAc 0.8 AAl 0.2 | 3.01 |
| 19 | 12 | 1 | 1 | 1 | 1 | 1 | 5.5 | 0.2 | 0.1 | 48.1 | 325 | 400 | 97.3 | 83.1 | 8.8 | | | | 0.99 |
| 20 | 12 | 1 | 1 | 1 | 1 | 1 | 5.5 | 0.2 | 0.1 | 48.1 | 425 | 3600 | 92.3 | 74.3 | 11.9 | | | | 7.96 |
| 21 | 12 | 1 | 1 | 1 | 1 | 1 | 5.5 | 0.2 | 0 | 47.8 | 375 | 1200 | 96.2 | 79.7 | 10.5 | | | | 2.85 |
| 22 | 12 | 1 | 1 | 1.5 | 0 | 1.5 | 5.5 | 0.1 | 0.1 | 47.9 | 375 | 1200 | 95.1 | 79.3 | 10.2 | | | | 2.83 |
| 23 | 12 | 1 | 1 | 1.5 | 1.5 | 0 | 5.5 | 0.1 | 0.1 | 47.9 | 365 | 1200 | 95.7 | 82.6 | 8.3 | 1.8 | 0.8 | | 2.95 |
| 24 | 12 | 1 | 1 | 0 | 1.5 | 1.5 | 5.5 | 0.1 | 0.1 | 47.9 | 375 | 1200 | 96.3 | 81.3 | 9.1 | | | | 2.91 |
| 25 | 12 | 1 | 4 | 1.5 | 1.5 | 0 | 6 | 0.1 | 1 | | 350 | 1200 | 94.2 | 82.5 | 6.7 | 1.9 | 1.0 | | 2.95 |
| 26 | 12 | 3 | 2 | 1.5 | 1.5 | 0 | 6 | 0.1 | 1 | | 400 | 1200 | 95.3 | 80.5 | 9.5 | 2.2 | 1.8 | | 2.88 |

Note: HAc, acetic acid; AAl, acetaldehyde.

EXAMPLE 27

A mixture of propylene, air and nitrogen in a molar ratio of 1:7:7 is fed with a space velocity of 1200 liter.-gas/liter.catalyst/hr into a reactor containing the same catalyst composition as in Example 1 at 350°C. The following results are obtained: propylene conversion, 90.9 %; acrolein yield, 74.3 %; acrylic acid yield, 5.7 %; carbon dioxide yield, 3.9 %; carbon monoxide yield, 2.2 %; acetaldehyde yield, 1.9 %.

EXAMPLES 28 TO 31

Using the catalyst compositions as in Examples 1, 8, 11 and 18, the vapor phase oxidation of propylene to acrolein is carried out continuously. The feed gas is a mixture of propylene, air and steam in a molar ratio of 1:7:7. The space velocity is 1200 liter.gas/liter.-catalyst/hr. The catalytic activity after 800 to 1000 hours from the start of the oxidation is shown in Table 2.

REFERENCE EXAMPLES 2 TO 12

Using various catalyst compositions not falling within the scope of the invention, the vapor phase oxidation of propylene to acrolein is carried out as in Example 1. The results are shown in Table 3.

Table 2

| Example No. | Catalyst composition | | | | | | | | | Reaction condition | | Propylene conversion (%) | Yield (%) | | | |
|---|---|---|---|---|---|---|---|---|---|---|---|---|---|---|---|---|
| | Mo | Bi | Fe | Mg | Co | Mn | Ni | Tl | P | O | Reaction temp. (°C) | Reaction time (hr) | | Acrolein | Acrylic acid | $CO_2$ | CO |
| 28 | 12 | 1 | 2 | 1.5 | 1.5 | 0 | 6 | 0.1 | 1 | 52.2 | 355 | 980 | 97.0 | 83.3 | 8.0 | 2.2 | 1.2 |
| 29 | 12 | 1 | 1 | 1 | 1 | 1 | 5.5 | 0.2 | 0.1 | 48.1 | 375 | 930 | 95.6 | 81.7 | 8.5 | | |
| 30 | 12 | 1 | 1 | 0 | 2 | 0 | 7 | 0.1 | 1 | 50.7 | 360 | 810 | 93.9 | 81.1 | 7.6 | | |
| 31 | 12 | 1 | 1 | 4 | 0 | 0 | 4.5 | 0.2 | 0.1 | 48.1 | 375 | 980 | 93.7 | 74.4 | 12.8 | 1.9 | 1.6 |

Table 3

| Reference Example No. | Catalyst composition | | | | | | | | | | Reaction condition | | Propylene conversion (%) | Yield (%) | | | | Space time yield (mol/l/hr) |
|---|---|---|---|---|---|---|---|---|---|---|---|---|---|---|---|---|---|---|
| | Mo | Bi | Fe | Mg | Co | Mn | Ni | Tl | P | O | Reaction temp. (°C) | Space velocity (l/l/hr) | | Acrolein | Acrylic acid | $CO_2$ | CO | |
| 2 | 12 | 1 | 1 | 0 | 0 | 0 | 8.5 | 0 | 0.1 | 47.8 | 400 | 1200 | 90.9 | 52.6 | 21.5 | 6.8 | 5.3 | 1.87 |
| 3 | 12 | 1 | 1 | 0 | 0 | 0 | 8.5 | 2.5 | 0.1 | 51.5 | 450 | 1200 | 45.3 | 26.5 | 2.4 | 6.9 | 6.7 | 0.95 |
| 4 | 12 | 1 | 1 | 4 | 0 | 0 | 4.5 | 0 | 0.1 | 47.8 | 400 | 1200 | 90.8 | 64.5 | 14.2 | 4.5 | 4.1 | 2.30 |
| 5 | 12 | 1 | 1 | 4 | 0 | 0 | 4.5 | 2.5 | 0.1 | 51.5 | 450 | 1200 | 41.8 | 20.3 | | | | 0.73 |
| 6 | 12 | 2 | 2 | 2.5 | 0 | 0 | 3 | 0 | 0.1 | 47.8 | 400 | 1200 | 90.0 | 60.5 | 14.0 | | | 2.16 |
| 7 | 12 | 1 | 1 | 0 | 2 | 0 | 7 | 2 | 1 | 53.5 | 475 | 1200 | 21.8 | 4.6 | | | | 0.16 |
| 8 | 12 | 1 | 1 | 0 | 4 | 0 | 4.5 | 0 | 0.08 | 47.5 | 400 | 1200 | 90.7 | 64.2 | 18.1 | 4.2 | 1.8 | 2.29 |
| 9 | 12 | 1 | 1 | 0 | 0 | 2 | 6.5 | 0 | 0.1 | 47.8 | 375 | 1200 | 91.4 | 57.6 | 19.1 | 5.1 | 3.4 | 2.06 |
| 10 | 12 | 1 | 1 | 0 | 0 | 2 | 6.5 | 2.5 | 0.1 | 51.5 | 475 | 1200 | 26.5 | 5.3 | | | | 0.19 |
| 11 | 12 | 1 | 1 | 1 | 1 | 1 | 5.5 | 0 | 0.1 | 47.8 | 400 | 1200 | 92.2 | 65.1 | 14.6 | 5.4 | 3.4 | 2.33 |
| 12 | 12 | 1 | 1 | 1 | 1 | 1 | 5.5 | 2 | 0.1 | 50.8 | 475 | 1200 | 17.8 | 3.4 | | | | 0.12 |

REFERENCE EXAMPLE 1

As in Example 1 but using no thallium, there is prepared a catalyst composition, of which the active components correspond to the formula: $Mo_{12}Bi_1Fe_2Ni_6Co_{1.5}Mg_{1.5}P_1O_{51.5}$ (wherein the carrier components are omitted). The vapor phase oxidation of propylene to acrolein is carried out as in Example 1 but at a reaction temperature of 400°C. The following results are obtained: propylene conversion, 90.1 %; acrolein yield, 59.5 %; acrylic acid yield, 16.6 %; carbon dioxide yield, 4.8 %; carbon monoxide yield, 3.5 %; acetic acid yield, .8 %; acetaldehyde yield, 2.5 %.

For comparison, some conventional catalyst compositions and their catalytic activities in the vapor phase oxidation of propylene to acrolein are shown in Table 4.

Table 4

| No. | Catalyst composition | | | | | | | Bath temperature (°C) | Contact time (sec) | Space velocity (l/l/hr) | Propylene conversion (%) | Yield (%) | | | | Space time yield (mol/l/hr) |
|---|---|---|---|---|---|---|---|---|---|---|---|---|---|---|---|---|
| | Mo | Bi | Fe | Co | Ni | P | O | | | | | Acrolein | Acrylic acid | $CO_2$ | C | |
| 1 | 12 | 1 | 1 | 0.3 | 10 | 1 | 51 | 310 | 4.6 | | 95.0 | 71.0 | 14.0 | | | 0.45 |
| 2 | 12 | 1 | 1 | 0.3 | 10 | 1 | 51 | 310 | | 200 | 95.0 | 71.0 | 14.0 | 5.1 | 1.9 | 0.45 |
| 3 | 12 | 1 | 1 | 2 | 7 | 1 | 53 | 365 | 7.2 | 89 – 128*) | 98.0 | 45.0 | 27.0 | | | 0.11– 0.15*) |
| 4 | 12 | 1 | 1 | 4 | 4.5 | 0.08 | 51 | 310 | 4 | 160 – 230*) | 95.5 | 72.1 | 6.0 | | | 0.30– 0.43*) |
| 5 | 12 | 2 | 2 | 0 | 7.5 | 1 | 55 | 310 | 3 | 220 – 310*) | 95.0 | 65.0 | 7.8 | | | 0.38– 0.53*) |

Note:
No. 1, U.S. patent 3,454,630 (Example 29);
No. 2, Japanese patent publication 5855/1969 (Example 1);
No. 3, U.S. patent 3,454,630 (Example 37);
No. 4, U.S. patent 3,522,299 (Example 32);
No. 5, U.S. patent 3,545,630 (Example 22);
*) assumed values.

From the above results, it can be understood that the kind and number of the component atoms in the catalyst composition of the invention are critical for exerting the advantageous catalytic activity in the vapor phase oxidation of propylene to acrolein.

What is claimed is:
1. A process for preparing acrolein by the vapor phase oxidation of propylene which comprises contacting propylene and oxygen with a catalyst composition consisting essentially of a catalyst system of the formula:

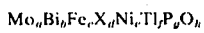

wherein X is one or more of Mg, Mn and Co and $a, b, c, d, e, f, g$ and $h$ represent, respectively, the number of atoms and wherein $a$ is 12, $b$ is 0.1 to 5, $c$ is 0.1 to 5, $d$ is 0 to 12, $e$ is 0.1 to 12, $f$ is 1 or less but not less than a catalytic amount, $g$ is 0 to 5 and $h$ is a number determined by the valence requirements of the other atoms and is 36 to 89 at a temperature from 200° to 550°C. and at a space velocity of 100 to 12,000 liter.gas/liter.catalyst/hr.

2. The process according to claim 1, wherein $a$ is 12, $b$ is 0.5 to 3, $c$ is 0.5 to 5, $d$ is 0 to 9, $e$ is 1.5 to 12, $f$ is 0.01 to 0.5, $g$ is 0.01 to 2 and $h$ is 39.1 to 74.8.

3. The process according to claim 1, wherein the contact is effected at a temperature of from 250° to 500°C.

4. The process according to claim 1, wherein the contact is effected under approximately atmospheric pressure.

5. The process according to claim 1, wherein the contact is effected at a space velocity of 200 to 6,000 liter.gas/liter.catalyst/hr.

6. The process according to claim 1, wherein the oxygen source is air.

7. The process according to claim 6, wherein the molar ratio of propylene and oxygen is 1: 0.4–3.

8. The process according to claim 1, wherein the contact is effected in the presence of steam.

9. The process according to claim 8, wherein the molar ratio of propylene and steam is 1:1–15.

10. The process according to claim 1, wherein said catalyst composition is incorporated with a carrier, the amount of the carrier being less than 90% by weight of the catalyst composition.

11. The process according to claim 10, wherein the amount of the carrier is 5 to 90% by weight of the catalyst composition.

* * * * *

UNITED STATES PATENT AND TRADEMARK OFFICE
CERTIFICATE OF CORRECTION

PATENT NO. : 3,970,702
DATED : July 20, 1976
INVENTOR(S) : Tatsuo SHIRAISHI et al It is certified that error appears in the above-identified patent and that said Letters Patent are hereby corrected as shown below:

IN THE HEADING OF THE PATENT:

In the list of Inventors, the name of the fourth inventor should read -- Shigeru Honmaru --

Signed and Sealed this

Twenty-ninth Day of March 1977

[SEAL]

Attest:

RUTH C. MASON
*Attesting Officer*

C. MARSHALL DANN
*Commissioner of Patents and Trademarks*